United States Patent
Weekman et al.

Patent Number: 5,419,884
Date of Patent: May 30, 1995

[54] REGENERATIVE MERCURY REMOVAL PROCESS

[75] Inventors: Vernon W. Weekman, Washington Crossing; Tsoung Y. Yan, Philadelphia, both of Pa.

[73] Assignee: Mobil Oil Corporation, Fairfax, Va.

[21] Appl. No.: 20,943

[22] Filed: Feb. 19, 1993

[51] Int. Cl.⁶ .............. B01D 15/04; B01D 53/04; C07C 7/13; C22B 43/00

[52] U.S. Cl. .................. 423/210; 208/253; 95/134; 210/673; 75/670

[58] Field of Search ............ 423/210; 502/34, 75; 75/710, 670; 95/134; 210/673; 208/253

[56] References Cited

U.S. PATENT DOCUMENTS

| | | | |
|---|---|---|---|
| 2,882,243 | 4/1959 | Milton | 423/718 |
| 2,982,612 | 5/1961 | Barrer et al. | 423/718 |
| 3,650,687 | 3/1972 | McDaniel et al. | 502/68 |
| 3,755,989 | 9/1973 | Fornoff et al. | 95/134 |
| 4,101,631 | 7/1978 | Ambrosini et al. | 423/210 |
| 4,230,486 | 10/1980 | Capuano et al. | 75/670 |
| 4,474,896 | 10/1984 | Chao | 502/216 |
| 4,874,525 | 10/1989 | Markovs | 210/673 |
| 4,892,567 | 1/1990 | Yan | 95/126 |
| 4,932,334 | 6/1990 | Patte et al. | 95/229 |
| 4,982,050 | 1/1991 | Gammie et al. | 423/210 |
| 5,053,209 | 10/1991 | Yan | 208/253 |
| 5,223,145 | 6/1993 | Markovs | 423/210 |
| 5,271,760 | 12/1993 | Markovs et al. | 95/134 |
| 5,281,258 | 1/1994 | Markovs | 95/134 |

FOREIGN PATENT DOCUMENTS 143631 9/1980 Germany .............. 75/710

OTHER PUBLICATIONS

Kirk-Othmer. "Encyclopedia of Chemical Technology", 3rd ed; vol. 13, pp. 678, 685, 690-692 (1981).

*Primary Examiner*—Gary P. Straub
*Assistant Examiner*—Peter T. DiMauro
*Attorney, Agent, or Firm*—A. J. McKillop; M. D. Keen

[57] ABSTRACT

A regenerative mercury removal process for simultaneously removing high mercury and water content from a fluid comprising; contacting for a sufficient time a high content mercury-containing fluid with an adsorbent bed having sufficient silver coated or impregnated thereon to remove therefrom substantial amounts of mercury and water; regenerating the adsorbent using a regenerative gas and condensing-out and recovering the mercury to yield a fuel substantially free from mercury.

21 Claims, 1 Drawing Sheet

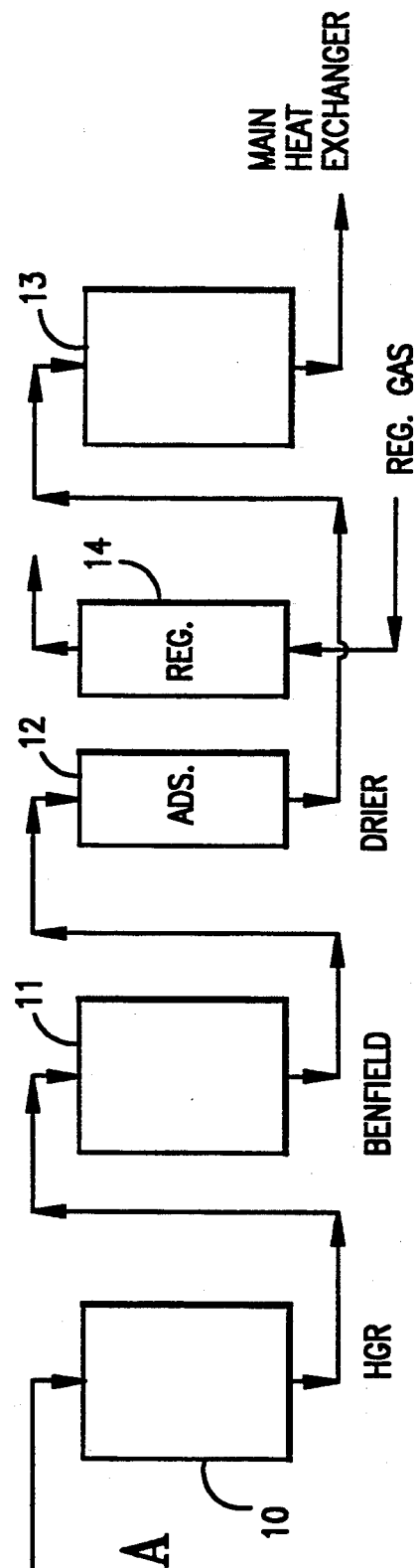
FIG. 1A  CONVENTIONAL SCHEME
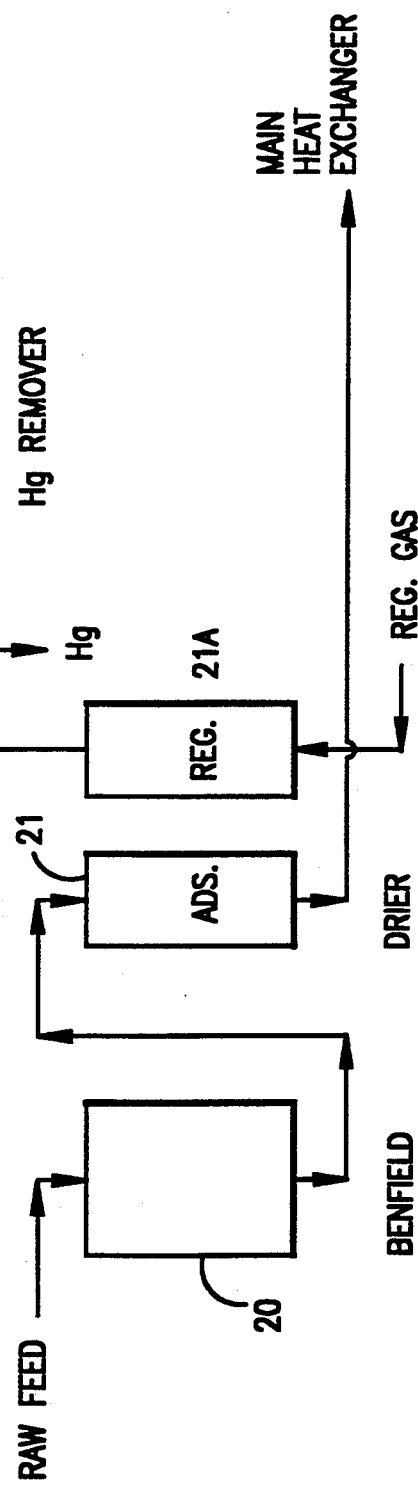
FIG. 1B  PROPOSED SCHEME

REGENERATIVE MERCURY REMOVAL PROCESS

BACKGROUND OF THE INVENTION

The present invention is directed to a method for removing high contents of mercury and water from fluids and eliminating the generation of mercury-containing disposal wastes. More particularly, this invention relates to a method of simultaneously removing high contents of mercury and water from natural gases, which allows for regeneration of the adsorbent, recovery of the captured mercury and direct use of the regeneration gas as fuel.

It is often desirable to simultaneously remove water and mercury from fluids, such as from hydrocarbon fluids, an example being natural gas. Simultaneous removal processes are described in U.S. Pat. No. 4,892,567 which is herein incorporated by reference. This patent describes a molecular sieve which is modified with gold or silver for the purpose of simultaneously removing mercury and water from fluids. Molecular sieves are disclosed in this reference, in particular zeolite A, as being useful for removing mercury and water and for being capable of being regenerated. This reference discloses the use of gold or silver in amounts of 0.001–15% by weight as a coating on or impregnation in the zeolite. No direct suggestion is given, however, for removing massive quantities of mercury from the fluid while providing for a regenerative process which allows for the recovery of useful mercury and low mercury-content regenerative gas useful as fuel.

Conventional methods of removing high amounts of mercury generally involve using sulfur on carbon mercury removal bed (S/C HGR) to remove the major amount of mercury. The disadvantage of this method, however, is that the spent adsorbent often contains up to 10% or more mercury and is not able to be regenerated. The used adsorbent must then be disposed of as waste, creating environmental concerns. Attempts to transport mercury wastes raise issues regarding regulations governing transportation of hazardous waste materials. In addition, conventional methods of removing high amounts of mercury from fluids usually involve a secondary mercury removal step prior to liquefaction. Conventional methods are often therefore inefficient and costly.

While U.S. Pat. No. 4,892,567 has disclosed a means for overcoming some of the disadvantages of the conventional mercury removal methods, it has not focused on regeneration whereby high amounts of mercury are substantially recoverable and the regeneration gas is useful as fuel. Thus, the present invention is an improvement over the teachings and disclosure of this patent.

Water is effectively removed from hydrocarbon fluids, such as natural gases, by means of molecular sieves, particularly the synthetic crystalline zeolite known as zeolite A.

Zeolite A contains cavities formed by sodalite cages stacked in simple cubic form. The sodalite cages are made up of a truncated octahedral having a silica or alumina tetrahedron at each point. The cavities are surrounded by eight oxygen atoms, and are partially blocked by cations that balance the charge on the oxygen atoms. In zeolite A, each alumina moiety is balanced by two positive charges. If the cation is sodium, the cavity is reduced to about 4.2 angstroms in diameter. If the cation is potassium, the cavity is reduced to about 3 angstroms in diameter. If the cation is calcium, the cavity is reduced to about 5 angstroms in diameter.

Zeolite A having sodium, potassium and calcium ions is known as zeolite 4A, zeolite 3A and zeolite 5A, respectively. The pore diameters of zeolite A make them especially suitable as drying agents, since the pores are large enough to accommodate water molecules, but not most other molecules found in nature. Zeolite A is further described in U.S. Pat. Nos. 2,882,243; 2,982,612; and 3,650,687. When a zeolite used for drying fluids becomes saturated with water, it must be regenerated, which is often accomplished by heating with flowing hot gas. Zeolite 4A is the most commonly used molecular sieve for drying natural gas.

In the inventive regenerative mercury removal process, it is preferred that the capacity for mercury removal is large enough so that all mercury contained in the fluid can be removed in the period during which the adsorbent becomes fully saturated with water and must be regenerated.

Natural gas may contain as much as 250 ppb (micrograms/m$^3$) mercury. Natural gas is, in many commercial liquefaction operations, transported to and cooled in aluminum heat exchangers. Mercury present in the natural gas causes corrosion of the aluminum and must be removed. Additionally, high contents of mercury cannot remain in the regenerative gas if it is to be used directly as fuel.

There are a number of methods for removing mercury from fluids such as gases. U.S. Pat. Nos. 4,101,631 and 4,474,896 describe the removal of mercury from gas streams by means of sulfur or sulfur compounds on supports such as zeolite an activated carbon. These methods are capable of reducing the level of mercury to about 0.1 ppb. Even this level of mercury in a stream, however, can injure aluminum heat exchangers.

There is a need to reduce the level of mercury in fluids to below 0.01 ppb or less. In order to be commercially feasible, the method must be inexpensive as well as efficient. It would be especially desirable to remove mercury and water simultaneously and repeatedly from a fluid with the same agent, so that, following contact with the agent, the level of mercury is less than 0.01 ppb and the level of water is less than 1 ppm. It is even further desirable, however, to find an effective and efficient means of removing high amounts of mercury from a fluid in a simplified one-step process, regenerating the adsorbent and recovering the mercury, thereby eliminating the need for disposal of mercury-containing adsorbent waste.

It is a principal object of the present invention to provide a means for removing and recovering high amounts of mercury from a fluid and providing a means for regenerating the adsorbent many times. A further object of the present invention is to simultaneously remove high amounts of mercury and water and regenerating the mercury such that the resultant regeneration gas can be used directly as fuel. The additional objective is to remove the mercury from the atmosphere and to recover the mercury as a valuable product. These and other objectives will become apparent to those of ordinary skill in the art.

SUMMARY OF THE INVENTION

The present invention relates to a regenerative mercury removal process for simultaneously removing high mercury and water content from a fluid, regenerating an adsorbent without generating mercury/adsorbent waste, eliminating mercury from entering the environment, recovering the mercury as a valuable product and providing a regeneration gas effluent sufficiently free of mercury to be useful as a fuel including:

(a) contacting a high-content mercury-containing fluid with an adsorbent bed having sufficient silver coated, mixed or impregnated thereon to remove therefrom substantially all mercury and water;

(b) regenerating the adsorbent using a regenerative gas at a temperature and flow rate sufficient to remove water and mercury; and (c) condensing out and recovering the mercury from the regeneration gas effluent to yield a fuel substantially free from mercury.

The inventive process also concerns a regenerative mercury removal process for simultaneously removing high amounts of mercury and water from a fluid comprising:

(a) contacting a mercury-rich fluid with a molecular sieve comprising zeolite A having sufficient silver coated, mixed or impregnated thereon for a time such that upon saturation of said sieve with water substantially all mercury is concurrently removed;

(b) regenerating the molecular sieve using a regenerative gas; and (c) condensing-out and recovering the mercury from said regenerative gas effluent to yield a substantially mercury-free fuel.

The present invention also relates to a method for regenerating a molecular sieve containing water and high contents of mercury whereby mercury is recoverable substantially without generating waste and the regenerative gas effluent is sufficiently free of mercury to be useful as a fuel comprising the steps of:

a) contacting the molecular sieve with a regeneration gas for a time and temperature sufficient to remove substantially all the water and mercury from said sieve;

b) passing the resultant regeneration gas effluent through a condenser to recover substantially all the mercury;

c) collecting the regeneration gas for use as fuel; and d) optionally further removing residual mercury from the regeneration gas.

BRIEF DESCRIPTION OF THE DRAWINGS

FIG. 1 illustrates the conventional and inventive natural gas purification schemes for removing high content mercury. Scheme A is the conventional, prior art process. Scheme B is the inventive process.

DETAILED DESCRIPTION OF THE INVENTION

The capacity of silver on zeolite A, for example, for mercury removal depends on the operating conditions, such as temperature, fluid superficial velocity, pressure, mercury content in the feed and other impurities in the feed such as $H_2S$. The superficial velocity of a gas is the velocity of the gas in a vessel for cross-sectional area of the vessel when it is empty. The actual velocity of a gas in a vessel containing, for example, zeolite molecular sieves will be greater than the superficial velocity.

For example, the capacity of silver on zeolite 4A for mercury removal is $7 \times 10^{-3}$ grams mercury/gram silver at a gas contact time of $3 \times 10^{-3}$ seconds. This occurs, for example, when the gas flow rate is 26.5 feet pre second through a bed 1" in depth. The gas contact time is the bed depth divided by the flow rate.

When the zeolite is saturated with water (i.e., about 20–25% by weight), the mercury adsorption rate is reduced by, for example, about 50%, although the mercury adsorption capacity is not significantly affected.

The amount of silver used depends largely on the amount of mercury present in the fluid, the amount of mercury to be removed from the fluid, the flow rate of the fluid through the bed, the contact time of the fluid with the porous adsorbent substrate and the ability of the substrate to be regenerated. The amount of silver to be added to zeolite A, for example, may be calculated on the basis of the ability of one gram of silver on zeolite A to remove $7 \times 10^{-3}$ grams of mercury from a fluid at a contact time of $3 \times 10^{-3}$ seconds. For example, the amount of silver in the zeolite A may be as low as about 0.01% and as high as about 15%. Preferably the silver is present in amounts of about 0.1 to about 5% by weight. As previously mentioned, the concentration of silver on the substrate can be proportionally adjusted with the amount of mercury-containing gas to be treated by the adsorbent, i.e. volume of gas to be treated/volume of adsorbent.

A useful guideline for determining the amount of silver to be added to the zeolite is to add approximately 10 to about 10,000 times the stoichiometric amount of silver necessary to remove enough mercury from a fluid during each cycle to reduce the mercury content to or below the level desired assuming one atom of silver removes one atom of mercury. Preferably, the amount of silver present is approximately 50 to about 5,000 times the stoichiometric amount necessary to reduce the mercury to or below the level desired.

The distribution of silver concentration within the adsorbent bed may vary depending on the specific application. For example, the concentration of silver on zeolite 4A may be uniform throughout the bed or the concentration may be present in a gradient distribution; for example, higher concentrations of silver gradually decreasing to lower levels of silver throughout the bed. In this manner, a layered effect in the bed is achieved. It is preferred that the higher silver concentrations be placed at the top of the adsorbent bed, where feedstock initially enters the adsorbent chamber, with gradual decreases in the concentration of silver toward the bottom of the bed. Silver concentrations of an adsorbent system having such a gradient are preferably about 5% at the top of the bed, gradually decreasing to about 0.1% at the bottom. Ag is mixed with 4A zeolite to achieve the desired overall Ag concentration. The ratio of Ag and A can vary throughout the bed.

Most preferred is an adsorbent system arrangement comprising Zeolite 4A/Ag, where about two to five concentration regions or layers of silver are present in the bed, with the higher silver concentration at the top of the bed where intake of feedstock begins and decreasing toward the bottom of the bed in the exit flow direction of the feedstock. Such an arrangement allows for the major portions of mercury to be removed upfront as the feedstock initially contacts the adsorbent.

Turning now to FIG. 1, Scheme A illustrates a conventional method of removing high amounts of mercury from a fluid, e.g. a natural gas. The raw feedstock containing, for example, 250 ppb mercury or more is first passed through a mercury removal unit (HGR) 10 which contains an adsorbent such as sulfur on active carbon (S/C) or sulfur on X sieves. A major portion of the mercury is removed by the adsorbent, e.g. 99.9% or more, but the spent adsorbent, containing as much as 10% by weight mercury, is not regenerable and must be disposed of as waste. The gas is then passed through a Benfield unit 11 to remove $CO_2$ and $H_2S$, then through a drying unit 12 containing an adsorbent to remove water and finally through a second HGR unit 13 to remove trace amounts of mercury before being sent to the main heat exchanger for liquefaction.

In the inventive process, illustrated in Scheme B of FIG. 1, the raw feedstock of natural gas is passed directly through a unit 20 which removes $CO_2$ and $H_2S$, such as a Benfield unit, and then through a drying unit 21 which contains molecular sieve desiccants with high levels of silver to remove massive amounts of mercury and water simultaneously. The molecular sieves may be selected from any number of types which have a high water adsorption capacity. Among those useful include zeolite 3A, zeolite 4A, zeolite 5A, X, Y and mordenite. Of particular usefulness is zeolite 4A and 3A. The molecular sieve is coated or impregnated with elemental silver in quantities sufficiently high enough to remove massive amounts of mercury. The total amount of silver in the molecular sieve bed should be about 10 to about 10,000 times the stoichiometric requirement to form Ag/Hg amalgamation. The preferred range is about 50 to about 5,000 times the stoichiometric requirement. The required amount of silver to be associated with the molecular sieve bed can be calculated by dividing the amount of silver required for mercury removal by the amount of sieves required for water removal.

Regeneration of the molecular sieve is shown as 21A, which comprises the mercury and water laden molecular sieve. Regeneration is preferably carried out in the presence of inert gases such as $H_2$, $N_2$, methane, ethane, natural gas and $CO_2$. A vertical heat exchanger is the preferred type of condenser. More than one heat exchanger can be used in series if desired. Regeneration gas such as methane, is then passed through the molecular sieve. The regeneration gas effluent contains extremely high contents of mercury. For example, the effluent may contain as much as 10,000,000 ppb of mercury. Generally, the regeneration gas effluent will contain on the order of 5 to 50 times more mercury than the raw feedstock. The effluent containing these massive amounts of mercury are then passed through condenser 23 where the mercury is cooled and recovered.

In a preferred embodiment of this invention, a major portion of the mercury is deposited on the top of the molecular sieve bed and consequently the mercury present in the regeneration gas effluent in the early stage of regeneration is very high, and may be as much as 1,000,000 ppb, which makes condensation and recovery of mercury easy. Any trace amounts of mercury remaining in the effluent after condensation can be optionally removed if necessary by conventional means such as by adsorbents on a suitable support. Examples include sulfur or silver, copper, gold, bismuth, tin or iron, as metals, oxides or sulfides deposited on supports such as zeolites, active carbon, alumina, silica-alumina, silica clay or other high surface area, high pore volume supports. Additional conventional methods of disposing of remaining mercury subsequent to the condensation step include, for example, scrubbing processes such as polysulfide scrubbing systems. Such systems are generally represented as an optional mercury remover unit 24 in FIG. 1.

Regeneration gas flow rate is preferably relatively low to maximize high mercury concentration in the off-gas. The gas flow rate can be gradually increased, however, to a more conventional level as the temperature is increased. Useful regeneration gas velocities (GHSV) to maximize mercury removal from the adsorbent are given below for a given temperature:

| Temperature °F. | GHSV (V/V hr.)* |
| --- | --- |
| 0–200 | 2,000–5,000 |
| 200–300 | 3,000–6,000 |
| 300–400 | 4,000–7,000 |
| 400–500 | 5,000–8,000 |
| 500+ | 6,000–10,000 |

*Gas volume at 1 atmosphere and 60° F.

In general, the adsorbent can be regenerated more efficiently in a shorter period of time at higher temperatures. The resulting effluent gas will be higher in mercury content and easier to recover mercury from. The regeneration should be conducted in the absence of oxygen (i.e., in an inert or reducing gas). If the fluid being dried is natural gas, the natural gas can conveniently constitute the inert gas. Preferably, the direction of gas flow for the regeneration step is the reverse of that for water and mercury removal.

The regeneration pressure may be in the range of about 0–1000 psi and preferably about 10–100 psi. The zeolite may be regenerated 100 times or more under these conditions.

The regeneration gases of the present invention, having passed through condenser 23, are sufficiently free of mercury such that they are capable of being used directly for fuel, thereby overcoming the shortcomings of conventional regeneration gas effluent.

As previously mentioned a zeolite A is the preferred porous substrate. The silver may be added to the zeolite A several ways. One method involves ion exchanging or impregnating zeolite A with an aqueous solution of a salt of silver that is sufficiently soluble in water, optionally calcining the treated zeolite A at elevated temperatures, for example, at about 200°–500° C., and reducing the silver ions or oxides in or on the zeolite. Ion exchange involves contacting the zeolite with a sufficient excess of a solution of the silver or gold salt for a sufficient amount of time to permit the silver ions to permeate the cavities of the zeolite and to replace the ions present in the cavities. Impregnation involves contacting the zeolite with the solution so that the silver ions from the solution remain on or near the surface of the zeolite. Impregnation may, for example, be conveniently accomplished by spraying. Impregnation is preferred. Some suitable silver salts that are sufficiently soluble in water include silver chlorate, silver perchlorate and silver nitrate. In the event gold is substituted for or used in combination with the silver, some suitable salts of gold that are sufficiently soluble in water include $AuCl_3$ and $Au(CN)_3$. The pH of solutions into which zeolite A comes into contact should be maintained at a ph>6 by adding an alkali such as NaOH, KOH or $NH_4OH$, $NH_4OH$ is preferred. Some suitable reducing agents include hydrogen gas or a hydrocarbon gas such as methane, ethylene, ethane, propylene, propane, butenes, butanes and mixtures thereof. Such gases require heating at elevated temperatures, for example, at 200°–400° C. The reduction can conveniently be accomplished simultaneously with the drying of the zeolite, which is usually carried out with hot natural gas. The reduction may also take place at room temperature with reducing agents such as formaldehyde.

Another method for preparing zeolite A containing silver is to mill the zeolite with $Ag_2O$ or other silver compounds capable of being converted into elemental silver. The milled zeolite is extruded, dried, optionally calcined and reduced to convert the silver compound to elemental silver. Still another method involves adding the silver and salt along with a suitable binder to the zeolite, then kneading the mixture and extruding it to form extrudates, pellets and the like.

Preferably, however, the silver is added to the zeolite A by means of impregnating the zeolite A with a solution of a silver salt that is sufficiently soluble in water and that decomposes directly to elemental silver upon heating. Suitable salts include silver salts of a carboxylic acid, such as silver acetate, silver propionate, silver lactate and silver salicylate. Silver acetate is preferred. Upon heating to a temperature to about 180°–500° C., the silver salt decomposes directly to elemental silver impregnated on the zeolite A. A minimum temperature of 200° C. is preferred. This decomposition may conveniently be accomplished when the zeolite is being activated for drying by heating.

For example, silver acetate is soluble in water to the extent of about 1%. In the impregnation operation as described above, zeolite A adsorbs approximately 30% of its weight in water. Accordingly, impregnating zeolite A with a saturated aqueous solution of silver acetate followed by removal of the water from the zeolite results in zeolite A containing 0.3% silver. The process can be repeated if a higher percentage of silver is desired. If it is desired to minimize the number of impregnation steps, more than 0.3% silver may be added to zeolite A by contacting the zeolite with a solution containing more silver salt of a carboxylic acid than the zeolite can adsorb, and evaporating the solvent. The salt solution used to impregnate the zeolite may also contain less than 1% of silver acetate if the amount of silver on the zeolite A is desired to be less than 0.3%.

The method of impregnation with a solution of the silver salt capable of decomposing directly to elemental silver, such as a carboxylic acid, may be applied directly to zeolite A that is already being used on-line in a dryer vessel to remove water from fluid. The solution is added directly to wet on-line zeolite A in a drying chamber. The aqueous solution of the silver will rapidly, essentially homogeneously, permeate through the zeolite. Upon heating to about 180°–500° C., a substantially homogeneous distribution of silver will be provided to the zeolite A.

Zeolite A containing elemental silver is less likely to lose its water-adsorbing properties when the silver is added by means of impregnation, particularly impregnation with a salt of a carboxylic acid such as silver acetate, followed by decomposition with heat than if the silver is added by means of ion exchange followed by reduction.

The zeolite A containing silver as described above may be used to remove water and mercury simultaneously from a fluid. The fluid may be liquid or gaseous. The temperature of the removal operation may advantageously be maintained between 0° and 300° C., preferably between 10° and 200° C., more preferably between 20° and 100° C. The gas hourly space velocity depends on the mercury level in the fluid, the amount of silver in the adsorbent, and the degree of mercury removal desired and may be as low as 1,000 v/v hr and as much as ten million v/v hr. The gas hourly space velocity is preferably 10,000–100,000 v/v hr. The pressure at which the simultaneous water and mercury removal and regeneration steps are conducted is not critical. Some suitable pressures for water and mercury removal include, for example, 0–2000 pounds, preferably 10–1000 pounds.

As previously mentioned, the amount of zeolite A in the water- and mercury-removing chamber and the amount of silver associated with the zeolite A depend upon the amount of water and mercury that is to be removed from the fluid and on the flow rate of the fluid through the zeolite. In a typical drying operation, about one pound of zeolite is estimated for each 0.1 pound of water to be removed. The amount of silver added to the zeolite depends on the gas contact time, the amount of mercury to be removed, as well as on other factors, as discussed above.

If the silver is added by decomposing a salt of carboxylic acid, the number of regenerations the silver-containing zeolite can tolerate without significantly losing its water adsorbing capacity does not depend upon the amount of silver in the zeolite. If, on the other hand, the silver is ion exchanged into the zeolite by means of salts such as $AgNO_3$, the regeneration conditions described above may lead to deterioration of the capacity of the zeolite for water at levels above about 1% Ag, and especially above about 5%.

The invention may be further understood with reference to the following non-limiting examples.

EXAMPLE I

Preparation of Silver on Zeolite 4A with Silver Acetate

A 0.1% aqueous silver acetate solution containing 0.03 g of silver acetate is added drop wise to 10 g of 40–60 mesh 4A molecular sieves. During addition, the sieves are mixed and tumbled to assure a uniform application of the silver. The excess water is vaporized from the sieves and the sieves are dried in a vacuum oven at 100° C. for 60 minutes to obtain a zeolite 4A adsorbent containing 0.3% silver.

Regeneration of zeolite 4A and Recovery of Mercury

A feedstock of natural gas containing high contents of mercury i.e., 100 ppb or more, and water is passed through the silver until the sieves reach a water saturation point, at which time they have preferably removed over 95% of mercury from the gas commensurate with the quantity of silver present in the sieve. A regeneration gas, in this case methane, is then passed through the sieve loaded with water and mercury at elevated temperatures to remove water and mercury. The direction of the regeneration gas through the sieve is the reverse of that for initial water and mercury removal from the feedstock. The flow rate and temperature of the regeneration gas is adjusted to each of the ranges previously disclosed with the result that substantially all the mercury and water is removed from the sieve. The regeneration gas effluent contains about 2,000,000 ppb mercury at the beginning of the regeneration cycle and drops to near zero at the end of the regenerative cycle. The effluent was then passed through a condenser unit comprising a vertical heat exchanger, whereby mercury is condensed-out and recovered from the boot at the bottom for use elsewhere and the effluent is sufficiently free of mercury to be useful as a commercial fuel.

The invention being thus described, it will be appreciated that the same may be varied in many ways. Such variations are not to be regarded as a departure from the spirit and scope of the invention and all such modifications are intended to be included within the scope of the following claims.

We claim:

1. A process for simultaneously removing mercury and water from a hydrocarbon fluid feedstock, regenerating an adsorbent bed, recovering mercury as a valuable product, and recovering and providing a regeneration gas effluent sufficiently free of mercury to be useful as a fuel comprising:
    a) contacting a mercury and water containing hydrocarbon fluid feedstock with a molecular sieve bed having an intake entrance area and an output exit area for said feedstock, said bed having silver associated therewith throughout wherein the concentration of silver is greatest at the entrance area being present in an amount of about 5% to about 15%, and decreases towards the exit area being present in an amount of about 0.01% to about 0.1%, said silver and said molecular sieve bed being present in an amount sufficient to remove substantially all the mercury and water from said hydrocarbon fluid feedstock;
    b) regenerating the bed using a regeneration gas at a temperature and flow rate sufficient to remove the water and mercury from said bed to produce a regeneration gas effluent containing said mercury and water; and
    c) condensing out and recovering substantially all the mercury from said regeneration gas effluent and yielding a regeneration gas substantially free from mercury for use as a fuel.

2. The process of claim 1, wherein the molecular sieve bed comprises a zeolite selected from the group consisting of zeolite 3A, zeolite 4A, zeolite 5A, zeolite X, zeolite Y and mordenite.

3. The process of claim 2, wherein the amount of silver present is at least stoichiometrically equivalent to the amount of mercury to be removed and mercury removal is accomplished concurrently with water uptake.

4. The process of claim 1, wherein the regeneration gas has a flow rate and temperature which is controlled to maximize a concentration and an amount of mercury in the effluent prior to mercury condensation.

5. The process of claim 4, wherein at least 90% of the mercury is removed from the mercury loaded adsorbent bed.

6. The process of claim 1, wherein the silver concentration is about 5% at the intake entrance area of the bed and decreases to about 0.1% at the output exit area of the bed.

7. The process of claim 1, wherein the adsorbent bed has from 2 to 5 layers each having a different concentration of silver.

8. The process of claim 1, wherein the condensation is carried out in a vertical heat exchanger.

9. The process of claim 8, wherein the heat exchanger contains a boot to collect mercury and to facilitate mercury recovery.

10. The process of claim 9, wherein residual amounts of mercury are further removed from said regeneration gas effluent by means of an adsorbent or scrubbing process.

11. The adsorbent process of claim 10, wherein the adsorbent for further removing residual amounts of mercury from said regeneration gas effluent is selected from the group consisting of silver based adsorbents, sulfur based adsorbents and mixtures thereof.

12. A regenerative mercury removal process for simultaneously removing about 95% or more of mercury and water from a hydrocarbon fluid feedstock and regenerating a molecular sieve adsorbent system comprising:
    a) contacting a mercury and water containing hydrocarbon fluid feedstock with a molecular sieve bed having an intake entrance area and an output exit area, said bed having silver associated therewith throughout wherein the concentration of silver is greatest at the intake entrance area being present in an amount of about 5% to about 15%, and decreases towards the exit area being present in an amount of 0.01% to about 0.1%, said silver and said molecular sieve bed being present in an amount sufficient to remove substantially all the mercury and water present in said hydrocarbon fluid feedstock;
    b) regenerating the bed using a regeneration gas at a temperature and flow rate sufficient to remove the water and mercury from said bed to produce a regeneration gas effluent containing said mercury and water, and
    c) condensing out and recovering substantially all the mercury from said regeneration gas effluent to yield a regeneration gas substantially free from mercury for use as a fuel.

13. The process of claim 12, wherein the hydrocarbon fluid feedstock is a gas.

14. The process of claim 12, wherein the hydrocarbon fluid feedstock is a liquid natural gas.

15. The process of claim 12, wherein the regeneration gas flow rate is about 1,000 to 10,000,000 V/V Hr.

16. The process of claim 15, wherein the regeneration temperature is about 100° F. to about 600° F.

17. The process of claim 12, wherein the molecular sieve bed is zeolite A.

18. The process of claim 12, wherein the regeneration gas is selected from the group consisting of $H_2$, methane, ethane and natural gas.

19. The process of claim 4, wherein the regeneration gas flow rate and temperature is one of the following ranges;

| Temperature °F. | GHSV (V/V hr.) at 1 atmosphere and 60° F. |
|---|---|
| 0–200 | 2,000–5,000 |
| 200–300 | 3,000–6,000 |
| 300–400 | 4,000–7,000 |
| 400–500 | 5,000–8,000 |
| 500+ | 6,000–10,000. |

20. The process of claim 1, wherein the regeneration gas is selected from the group consisting of $H_2$, methane, ethane and natural gas.

21. The process of claim 12, wherein the regeneration gas flow rate and temperature is one of the following ranges:

| Temperature °F. | GHSV (V/V hr.) at 1 atmosphere and 60° F. |
|---|---|
| 0–200 | 2,000–5,000 |
| 200–300 | 3,000–6,000 |
| 300–400 | 4,000–7,000 |
| 400–500 | 5,000–8,000 |
| 500+ | 6,000–10,000. |

* * * * *